United States Patent
Locke et al.

(10) Patent No.: US 9,204,801 B2
(45) Date of Patent: Dec. 8, 2015

(54) SYSTEMS, DEVICES, AND METHODS FOR IDENTIFYING PORTIONS OF A WOUND FILLER LEFT AT A TISSUE SITE

(71) Applicant: KCI Licensing, Inc., San Antonio, TX (US)

(72) Inventors: Christopher Brian Locke, Bournemouth (GB); Timothy Mark Robinson, Basingstoke (GB); Jonathan Paul Jaeb, Boerne, TX (US)

(73) Assignee: KCI Licensing, Inc., San Antonio, TX (US)

( * ) Notice: Subject to any disclaimer, the term of this patent is extended or adjusted under 35 U.S.C. 154(b) by 385 days.

(21) Appl. No.: 13/679,937

(22) Filed: Nov. 16, 2012

(65) Prior Publication Data
US 2013/0131471 A1 May 23, 2013

Related U.S. Application Data

(60) Provisional application No. 61/562,270, filed on Nov. 21, 2011.

(51) Int. Cl.
*A61F 13/00* (2006.01)
*A61B 5/00* (2006.01)
(Continued)

(52) U.S. Cl.
CPC ......... *A61B 5/0071* (2013.01); *A61F 13/00059* (2013.01); *A61L 15/42* (2013.01); *A61L 15/425* (2013.01); *A61M 1/0088* (2013.01)

(58) Field of Classification Search
CPC .... A61B 19/50; A61B 19/5244; A61B 19/56; A61B 2019/502; A61B 2019/505; A61B 2019/507; A61B 2019/5251; A61B 2019/5272; A61B 2019/5291; A61B 2019/562; A61B 2019/564; A61B 2019/566; A61B 5/0071; G06F 3/0317; G06F 3/014; G06F 3/03545; G06F 2203/04809; G06F 3/002; G06F 3/017; G06F 3/018; G06F 3/0202; G06F 3/0219; G06F 3/0395; G06F 3/04883; G06F 3/04886
USPC ....................... 600/407; 602/41–54
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 8/1982
AU 745271 4/1999
(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).

(Continued)

*Primary Examiner* — Michael Brown (57) ABSTRACT

Methods for treating a wound include positioning a wound filler having a coating agent containing a fluorescent material proximate the wound. The wound filler is removed after a time period. The wound is then scanned using a fluorescence scanner to determine whether a portion of the wound filler remains at the wound. In response to the portion of the wound filler remaining at the wound, the portion of the wound filler is removed. Other methods and systems are presented.

9 Claims, 6 Drawing Sheets

(51) Int. Cl.
*A61L 15/42* (2006.01)
*A61M 1/00* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0171924 A1* | 9/2004 | Mire et al. ............... 600/407 |
| 2008/0033324 A1 | 2/2008 | Cornet et al. |
| 2009/0182577 A1* | 7/2009 | Squilla et al. ............... 705/2 |
| 2009/0234217 A1* | 9/2009 | Mire et al. ............... 600/407 |
| 2009/0261171 A1* | 10/2009 | Lapstun et al. ........ 235/462.44 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 296 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2011/049522 A1 | 4/2011 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (copy and certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow. U.S.S.R. 1967 (copy and certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
International Search Report and Written Opinion for corresponding PCT/US2012/065661, mailed Apr. 29, 2013.

\* cited by examiner

SYSTEMS, DEVICES, AND METHODS FOR IDENTIFYING PORTIONS OF A WOUND FILLER LEFT AT A TISSUE SITE

CROSS-REFERENCE TO RELATED APPLICATION

This application claims priority to U.S. Provisional Patent Application No. 61/562,270 filed Nov. 21, 2011, entitled SYSTEMS, DEVICES, AND METHODS FOR IDENTIFYING PORTIONS OF A WOUND FILLER LEFT AT A TISSUE SITE, the disclosure of which is hereby incorporated by reference in its entirety.

BACKGROUND OF THE INVENTION

1. Field of the Invention

The present disclosure relates generally to medical treatment systems and, more particularly, but not by way of limitation, to systems, methods, and apparatuses for treating a tissue site with reduced pressure involving identifying portions of a wound filler left at a tissue site.

2. Description of Related Art

Clinical studies and practice have shown that providing a reduced pressure in proximity to a tissue site augments and accelerates the growth of new tissue at the tissue site The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a manifold device, or wound filler, such as a porous pad. The porous pad contains cells or pores that distribute reduced pressure to the tissue and channel fluids that are drawn from the tissue.

SUMMARY

According to an illustrative embodiment, a method for treating a wound includes positioning a wound filler having a coating agent containing a fluorescent marker proximate the wound. The wound filler is removed after a time period. The wound is then scanned using a fluorescence scanner to determine whether a portion of the wound filler remains at the wound. In response to the portion of the wound filler remaining at the wound, the portion of the wound filler is removed.

According to another illustrative embodiment, a method of treating a tissue site on a patient with reduced pressure includes deploying a manifold treated with a fluorescent dye proximate the tissue site. The manifold and a portion of intact epidermis of the patient is covered with a sealing member to form a sealed space in which the manifold is disposed. The sealing member has a first side and a second, tissue-facing side. A reduced pressure interface is fluidly coupled to the first side of the sealing member, wherein the reduced pressure interface is in fluid communication with the manifold and the tissue site. A reduced pressure source is fluidly coupled to the reduced pressure interface and reduced pressure is applied to the manifold. The manifold is removed after a predetermined time period. The tissue site is then scanned using a fluorescence scanner to determine whether a portion of the manifold remains at the tissue site. In response to the portion of the manifold remaining at the tissue site the portion of the manifold is removed.

According to another illustrative embodiment, a method for treating a wound includes positioning a wound filler having a coating agent containing fluorescent markers proximate the wound. The wound filler is removed after a time period. The wound is then scanned using a first mode of a fluorescence scanner to determine whether a portion of the wound filler remains at the wound. Responsive to an indication from the fluorescence scanner that the portion of the wound filler remains at the wound, the wound is scanned using a second mode of the fluorescence scanner. The portion of the wound filler is removed.

According to still another illustrative embodiment, a dressing for providing an indication when a portion of a dressing body has been left at a tissue site includes the dressing body comprising a reticulated foam for distributing reduced pressure to the tissue site. A fluorescent marker is attached to the dressing body such that the fluorescent marker provides an indication that the portion of the dressing body has been left at the tissue site when a fluorescence scanner is applied to the fluorescent marker.

According to another illustrative embodiment, a fluorescence scanner for identifying a portion of a wound filler left at a tissue site includes a pulsing mode causing the fluorescence scanner to emit a pulsing light and a continuous mode causing the fluorescence scanner to emit a continuous light. The pulsing light is brighter than the continuous light.

According to another illustrative embodiment, a system for identifying a portion of a wound filler left at a tissue site includes a scanner and the wound filler treated with a coating agent. The coating agent is operable to provide a visual indication when subjected to the scanner. The visual indication shows a location of the portion of the wound filler in the tissue site.

According to another illustrative embodiment, a system for identifying a portion of a wound filler left at a tissue site includes a scanner configured to emit light having a first wavelength. The wound filler is treated with a coating agent that is operable to absorb light from the scanner and consequently emit light having a second wavelength different from the first wavelength. The system further includes a receiver unit connected to the scanner for detecting light emitted by the coating agent, and a controller connected to the scanner and the receiver unit for managing the scanner and the receiver unit based on scanner settings and a feedback from the receiver unit. The system also includes an indicator connected to the controller that is operable to provide a visual or audio indication when the receiver unit detects the light emitted by the coating agent.

According to yet another illustrative embodiment, a reduced pressure treatment system for treating a tissue site with reduced pressure includes a fluorescence scanner and a wound filler treated with a coating agent. The coating agent is operable to provide a visual indication when subjected to the fluorescence scanner. The system further includes a sealing member for forming a fluid seal over the wound filler and a reduced-pressure source for at least temporarily fluidly coupling to the wound filler.

Other features and advantages of the illustrative embodiments will become apparent with reference to the drawings and detailed description that follow.

DETAILED DESCRIPTION OF ILLUSTRATIVE EMBODIMENTS

In the following detailed description of illustrative embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

Figure 1:
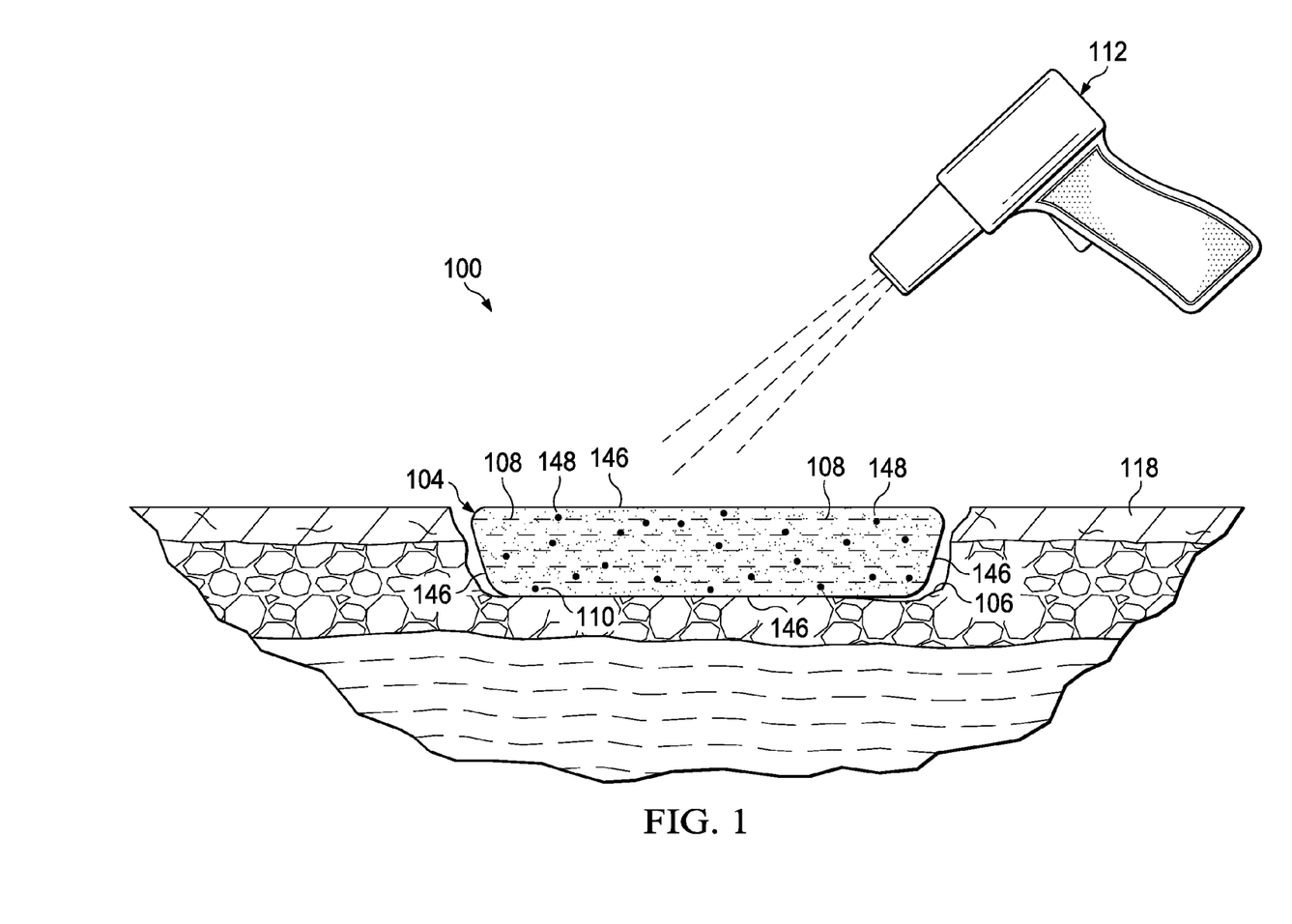
FIG. 1 is a cross-sectional view of an illustrative embodiment of a system for identifying residual portions of a wound filler left at a tissue site.
Figure 3:
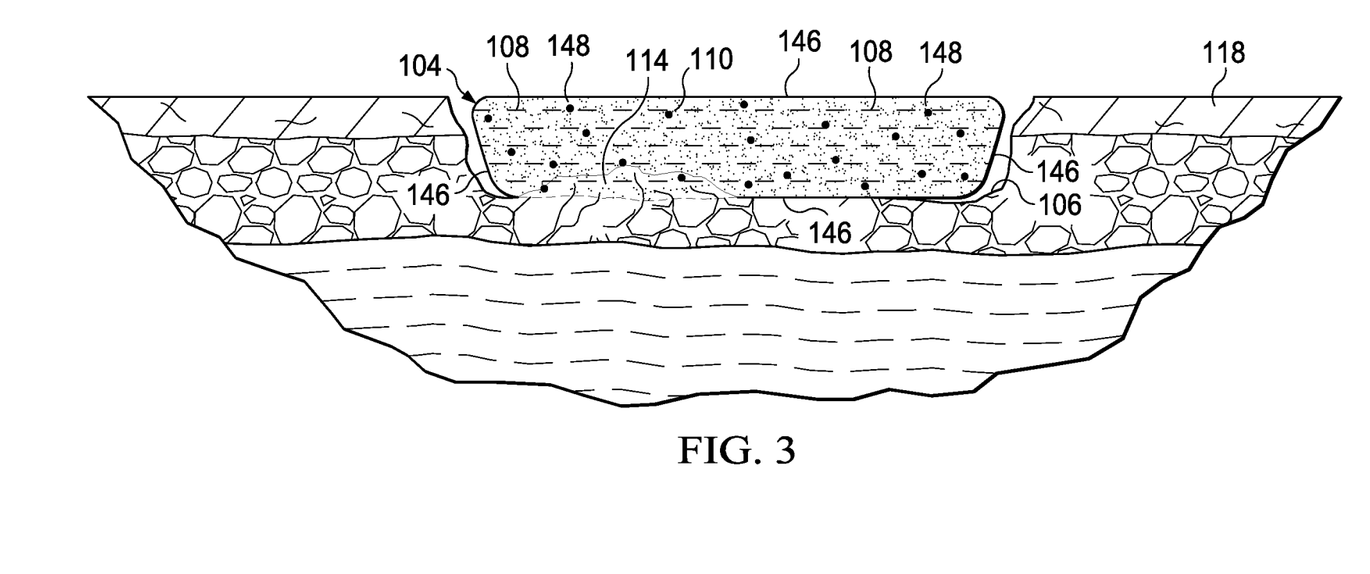
FIG. 3 is a cross-sectional view of the wound filler of FIG. 1 showing a portion of the wound filler with tissue in-growth.
Figure 4:
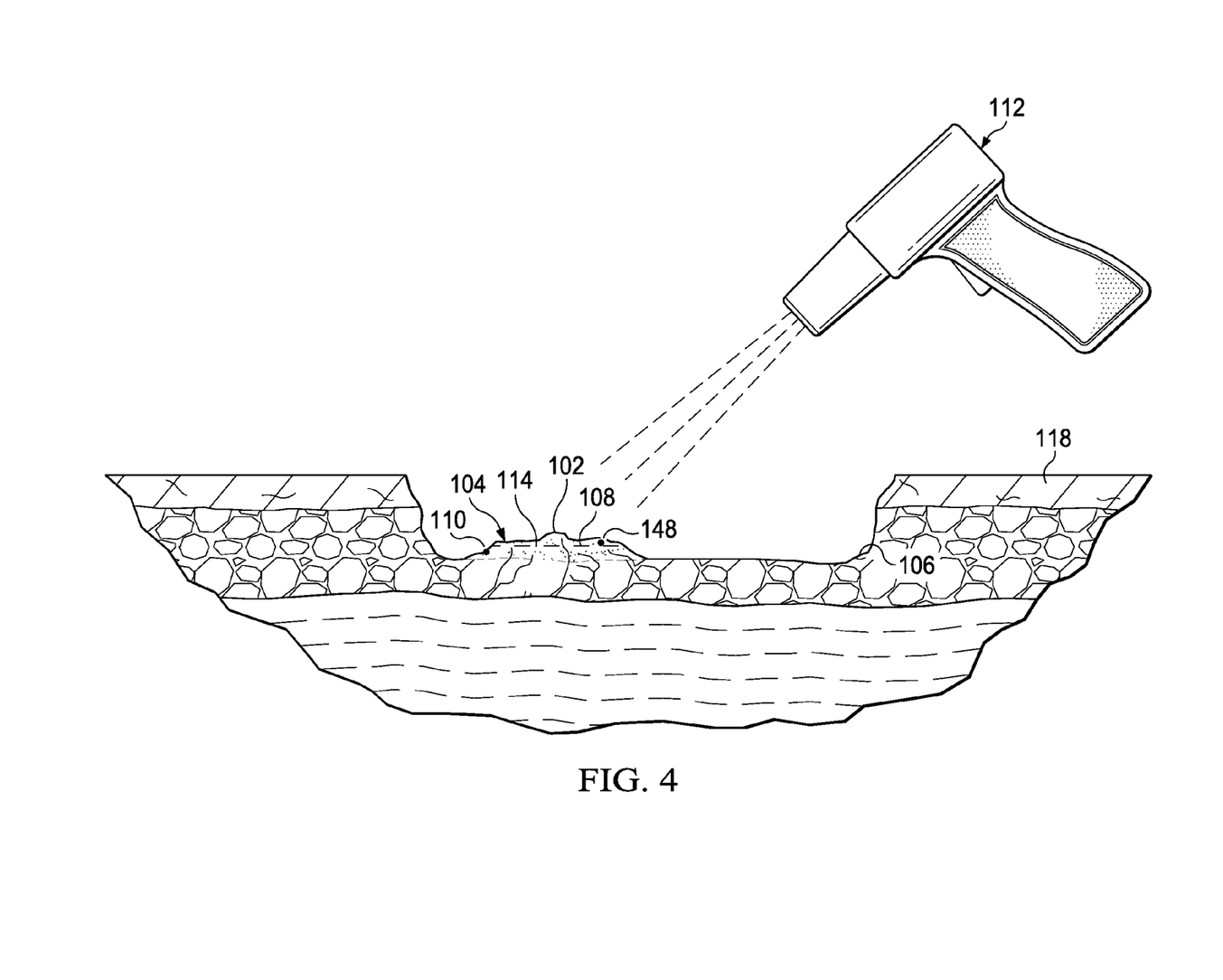
FIG. 4 is a cross-sectional view of the portion of the wound filler with tissue in-growth of FIG. 3 left at the tissue site after the wound filler has been removed.

Referring now to the drawings and initially to FIGS. 1, 3 and 4, a system 100 is presented for identifying one or more residual portions 102 of a wound filler 104 that may be left at a tissue site 106. The residual portions 102 of the wound filler 104 may be left subsequent to exposing the tissue site 106 to the wound filler 104 and then removing the wound filler 104 from the tissue site 106. The system 100 includes the wound filler 104 treated with a coating agent 108 containing markers 110. The system 100 further includes a scanner 112 for causing the markers 110 to become visible to a healthcare provider.

The wound filler 104, alternatively described as a dressing body, is placed proximate the tissue site 106 as part of a process for treating the tissue site 106. As will be described in more detail below, one process for treating the tissue site 106 may include applying reduced pressure to the tissue site 106 using a reduced pressure treatment system. Should the tissue site 106 be exposed to the wound filler 104 for too long of a time, or should other conditions be present, the tissue site 106 may begin to assimilate the wound filler 104, resulting in the wound filler 104 having tissue in-growth 114. In the event the wound filler 104 has the tissue in-growth 114, the wound filler 104 may tear when the wound filler 104 is removed from the tissue site 106, leaving behind the one or more residual portions 102 of the wound filler 104. Without aid, the one or more residual portions 102 of the wound filler 104 may not be readily visible to the human eye as the one or more residual portions 102 may be concealed by the tissue in-growth 114. Should the one or more residual portions 102 of the wound filler 104 be left in the tissue site 106, the one or more residual portions 102 may cause infection. The system 100 provides a means for identifying the one or more residual portions 102 of the wound filler 104 left in the tissue site 106 using the scanner 112 to excite the markers 110, attached to the one or more residual portions 102 of the wound filler 104, into producing light visible to a healthcare provider.

The system 100 may be used with various different types of tissue sites 106. The tissue site 106 may be a wound or wound cavity. As shown in at least FIGS. 1-4, the tissue site 106, may be through an epidermis 118 and into a subcutaneous tissue or any other tissue. The tissue site 106 may be the bodily tissue of any human, animal, or other organism, including bone tissue, adipose tissue, muscle tissue, dermal tissue, vascular tissue, connective tissue, cartilage, tendons, ligaments, body cavity or any other tissue.

The system 100 includes the wound filler 104 treated with the coating agent 108 containing the markers 110. The wound filler 104 is a biocompatible material that is capable of being placed in contact with the tissue site 106. Examples of the wound filler 104 may include, without limitation, devices that have structural elements arranged to form flow channels, such as, for example, cellular foam, open-cell foam, porous tissue collections, liquids, gels, and foams that include, or cure to include, flow channels. The wound filler 104 may be porous and may be made from foam, gauze, felted mat, or any other material suited to a particular biological application. In one embodiment, the wound filler 104 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. The porous foam may also be formed with a polyvinyl alcohol (PVOH) substrate.

Figure 5:
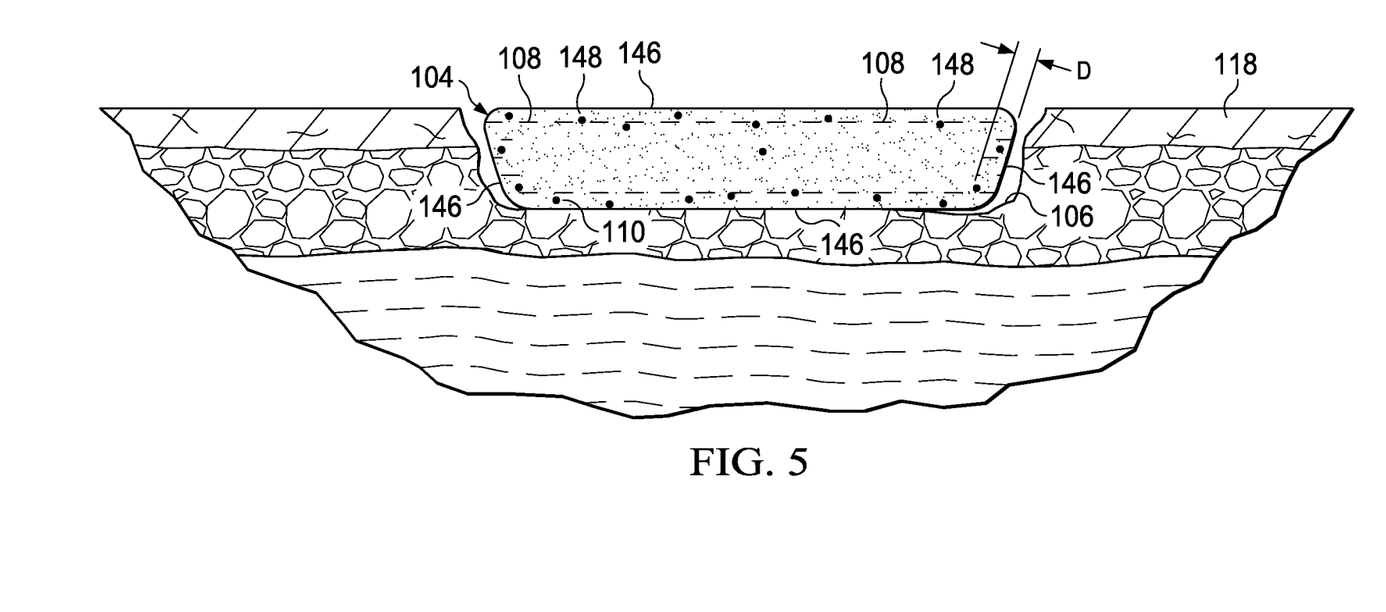
FIG. 5 is a cross-sectional view of an alternative embodiment of a wound filler.

The markers 110 may be fluorescent markers 148. The fluorescent markers 148 may include fluorescent dyes and pigments such as infrared or ultraviolet dyes and pigments. In one embodiment, the fluorescent markers 148 may be a polyvinyl alcohol (PVOH) carrier. The fluorescent markers 148 emit visible light when the fluorescent markers 148 absorb light or electromagnetic radiation of a different wavelength than the emitted visible light. As used herein, "visible light" refers to light visible to the unaided eye of a healthcare provider Referring now to FIGS. 1-5, the markers 110 may be embedded or integrated throughout the wound filler 104 as indicated in FIGS. 1-4. The coating agent 108 may be applied during the formation of the wound filler 104 such that the markers 110 form an integral part of the wound filler 104. In one embodiment, the markers 110 are grafted into the wound filler 104. Alternatively, as shown in FIG. 5, the markers 110 may only extend a certain depth, D, into the wound filler 104 from a surface 146 of the wound filler 104. In an illustrative, non-limiting embodiment, the markers 110 may extend to a depth of approximately 5 mm from the surface 146. The depth to which the markers 110 extend may depend on the type of fluorescent markers 148 used, e.g., infrared versus ultraviolet dyes, and the process used for applying the markers 110 to the wound filler 104. For example, the coating agent 108 may be adapted such that the coating agent 108 is applied to the surface 146 by process of dip coating or spray coating. In one embodiment, the coating agent 108 is applied through a plasma coating process. For example, the coating agent 108 may be a liquid that is sprayed onto the wound filler 104. Alternatively, the coating agent 108 may be a liquid that the wound filler 104 is immersed in for a time. The wound filler 104 may be dried or excess liquid may be removed from wound filler 104 after the coating agent 108 has been applied to the wound filler 104. For example, excess liquid may be removed by squeezing or compressing the wound filler 104. In one embodiment, the coating agent 108 is applied to the wound filler 104 after the wound filler 104 has been manufactured. Applying the coating agent 108 to the wound filler 104 which has already been manufactured simplifies the manufacturing process of the wound filler 104. However, the fluorescent markers 148 may only extend to the depth, D, from the surface 146. A healthcare provider should take note of whether the wound filler 104 only has the fluorescent markers 148 extending to the depth, D, should the healthcare provider cut the wound filler 104 for sizing to a particular wound. In one embodiment, the coating agent 108 may include a lubricant that attaches to the wound filler 104. The lubricant is adapted to ease the removal of the one or more residual portions 102 from the tissue site 106 should the one or more residual portions 102 be left in the tissue site 106. Instead of a healthcare provider having to cut or debride the tissue site 106 to remove the one or more residual portions 102, the lubricant may instead allow the healthcare provider to remove the one or more residual portions 102 using tweezers, thereby causing less trauma to the tissue site 106.

The system 100 further includes the scanner 112 for exciting the markers 110. In one example, the scanner 112 may be referred to as a fluorescence scanner. The scanner 112 may be a hand held device as shown in FIG. 1. The scanner 112 is light weight and compact such that the scanner 112 is easily handled and moved by a healthcare provider. The scanner 112 may be applied at a patient's point of treatment. In other words, attributes of the scanner 112 may allow the scanner 112 to be brought to the patient versus the patient needing to be transported to a scanner, e.g., a magnetic resonance imaging (MRI) machine. The scanner 112 emits light or electromagnetic radiation to excite or activate the fluorescent markers 148 into emitting light in the visual region. As previously described, the fluorescent markers 148 are adapted to emit visible light when the fluorescent markers 148 absorb radiation of a different wavelength than the emitted visible light. Thus, the scanner 112 is equipped to emit radiation of a wavelength sufficient to excite the fluorescent markers 148 into, emitting visible light. The visible light is a different wavelength than the wavelength being emitted by the scanner 112 and, thus, absorbed by the fluorescent markers 148. In one embodiment, the scanner 112 is adapted to emit infrared light with wavelengths in a range of about 700 nm to 900 nm. Infrared light with wavelengths in the range of about 700 nm to 900 nm may penetrate tissue up to 5 mm to excite the fluorescent markers 148 into emitting visible light perceivable by a health care provider. The scanner 112 may also be configured to emit the light with varying degrees of brightness. In one specific, non-limiting embodiment, the light may be emitted at less than 200 lux (lx). In another embodiment, the light may be emitted at greater than 600 lx. The depth the scanner 112 penetrates the tissue may depend on the light wavelength, the brightness of the light, and the type of tissue being treated.

The scanner 112 may be configured to have two different modes of operation. The first mode may be a pulsing mode. The pulsing mode causes the scanner 112 to emit a pulsing light. Pulsing the light emitted from the scanner 112 may allow the scanner 112 to emit brighter light than light that is continuously emitted without damaging the scanner 112. Brighter light requires a greater power draw from the scanner 112. Therefore, pulsing the brighter light only requires short bursts of high power output rather than a continuous high power output that could damage the scanner 112. In one specific, non-limiting embodiment, the light is pulsed between 0.5 to 2 Hertz (Hz). In another specific, non-limiting embodiment, the light is pulsed around 1 kHz. The light may be pulsed at a frequency not commonly found in the environment the scanner 112 is operating. To provide context, overhead lights and computers typically emit light at 60 Hz and 120 Hz and operate in an environment with electromagnetic noise of 60, 120, and 180 Hz. The pulsing light may have wavelengths in the range of 600 nm to 900 nm. The pulsing light may also have a brightness of greater than 600 lx. Increasing the brightness of the light emitted from the scanner 112 typically correlates to the fluorescent markers 148 absorbing more energy. Typically, the more energy the fluorescent markers 148 absorb, the brighter the light the fluorescent markers 148 will emit.

The second mode may be a continuous mode. The continuous mode causes the scanner 112 to emit a continuous light. In one embodiment, the continuous mode may cause the scanner 112 to emit the continuous light at less than 200 lx with a wavelength in the range of 700 nm to 900 nm. The pulsing light emitted in the first, pulsing mode will generally be brighter and contain more energy than the continuous light. The fluorescent markers 148 will absorb the continuous light emitted from the scanner 112 and, in return, emit a continuous light.

In one embodiment, the tissue site 106 may be scanned using the first mode of the scanner 112 to narrow down the area in which the residual portions 102 of the wound filler 104 may remain. The scanner 112 may then be used in the second mode proximate the area in which the residual portions 102 were located using the first mode. The continuous light emission in the second mode may make it easier for the healthcare provider to remove the residual portions 102 of the wound filler 104.

Figure 2:
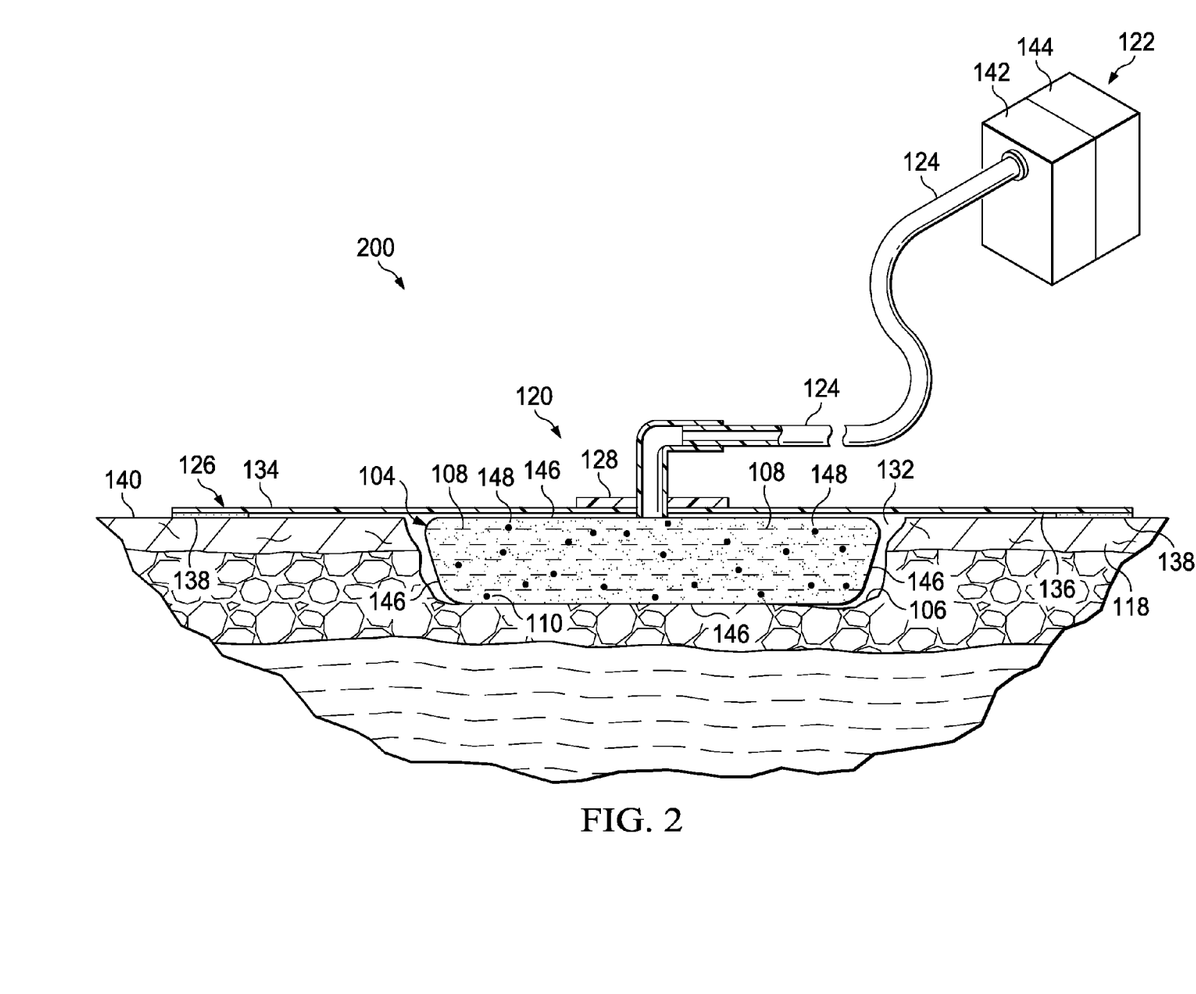
FIG. 2 is a cross-sectional view of an illustrative embodiment of a reduced pressure treatment system using the wound filler of FIG. 1 for treating a tissue site with reduced pressure.

Referring now to FIG. 2, a reduced-pressure treatment system 200 used in a process for treating the tissue site 106 with reduced pressure is presented. The system 200 includes a reduced-pressure dressing 120 for disposing proximate the tissue site 106. The system 200 also includes a reduced-pressure treatment unit 122 fluidly connected to the reduced-pressure dressing 120 through a reduced-pressure delivery conduit 124 for applying reduced pressure to the tissue site 106. The reduced-pressure dressing 120 includes the wound filler 104, a sealing member 126, and a reduced-pressure interface 128.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Unless otherwise indicated, values of pressure stated herein are gauge pressures. References to increases in reduced pressure typically refer to a decrease in absolute pressure, and decreases in reduced pressure typically refer to an increase in absolute pressure.

When used in the reduced-pressure treatment system 200, the wound filler 104 may be described as a manifold. The term "manifold" as used herein generally refers to a substance or structure that is provided to assist in applying reduced pressure to, delivering fluids to, or removing fluids from the tissue site 106. In some situations, the manifold may also be used to distribute fluids such as medications, antibacterials, growth factors, and various solutions to the tissue site 106. Other layers may be included in or on the manifold, such as absorptive materials, wicking materials, hydrophobic materials, and hydrophilic materials.

The wound filler 104 may be covered by the sealing member 126, which may also be referred to as a drape. The sealing member 126 forms a sealed space 132 over the tissue site 106. The sealing member 126 has a first side 134, and a second, tissue-facing side 136. The sealing member 126 may be any material that provides a fluid seal. "Fluid seal," or "seal," means a seal adequate to maintain reduced pressure at a desired site given the particular reduced-pressure source or subsystem involved. The sealing member 126 may, for example, be an impermeable or semi-permeable, elastomeric material.

An attachment device 138 may be used to hold the sealing member 126 against a portion of the patient's intact epidermis 140 or another layer, such as a gasket or additional sealing member. The attachment device 138 may take numerous forms. For example, the attachment device 138 may be a medically acceptable adhesive, such as a pressure-sensitive adhesive, that extends about a periphery or all of the sealing member 126. The attachment device 138 may also be a sealing ring or other device. The attachment device 138 is disposed on the second, tissue-facing side 136 of the sealing member 126. Before use, the attachment device 138 may be covered by a release liner (not shown).

The reduced-pressure interface 128 may be positioned adjacent to or coupled to the first side 134 of the sealing member 126 to provide fluid access to the wound filler 104. Another attachment device (not shown) similar to the attachment device 138 may be used to hold the reduced-pressure interface 128 against the sealing member 126. The reduced-pressure delivery conduit 124 fluidly couples the reduced-pressure treatment unit 122 and the reduced pressure interface 128. The reduced-pressure interface 128 allows the reduced pressure to be delivered to the tissue site 106. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

The reduced-pressure delivery conduit 124 may be a multi-lumen conduit or a single lumen conduit. It should be understood that the reduced-pressure delivery conduit 124 may be in many forms. The reduced-pressure delivery conduit 124 transports fluids from the reduced-pressure interface 128 to the reduced-pressure treatment unit 122. Liquids or exudates communicated from the wound filler 104 through the reduced-pressure delivery conduit 124 are removed from the reduced-pressure delivery conduit 124 and retained within a liquid-collection chamber (not explicitly shown) in fluid communication with the reduced-pressure treatment unit 122.

The reduced-pressure treatment unit 122 includes a reduced-pressure source 142 and an instrumentation unit 144. In one embodiment, the reduced-pressure source 142 is an electrically-driven vacuum pump. In another implementation, the reduced-pressure source 142 may instead be a manually-actuated or manually-charged pump that does not require electrical power. The reduced-pressure source 142 instead may be any other type of reduced-pressure pump, or alternatively a wall suction port such as those available in hospitals and other medical facilities. The instrumentation unit 144 may include sensors, processing units, alarm indicators, memory, databases, software, display units, and user interfaces that further facilitate the application of reduced-pressure treatment to the tissue site 106.

In one method of operation, a method for treating the tissue site 106 may include positioning the wound filler 104 having the coating agent 108 containing the fluorescent markers 148 proximate the tissue site 106. After a time period, e.g., after 20 hours or more, the wound filler 104 is removed from the tissue site 106. The time period depends on the expected rate of granulation formation. It is preferred that the wound filler 104 be removed prior to significant amounts of tissue growing into the wound filler 104 such that new tissue growth is not torn out of the tissue site 106 when the wound filler 104 is removed. In specific, non-limiting examples, the time period may be 12 hours, 20 hours, one day, two days, five days or more. It should be appreciated, however, that the time period depends on the patient, the type of wound, and whether reduced pressure therapy is being applied. While reduced pressure therapy may augment or accelerate the growth of new tissue, the method of operation may be used with or without reduced pressure therapy.

After the wound filler 104 has been removed, the tissue site 106 is scanned using the scanner 112 to determine whether the one or more residual portions 102 of the wound filler 104 remain at the tissue site 106. As described above, should the tissue site 106 be exposed to the wound filler 104 for too long of a time, the tissue site 106 may begin to assimilate the wound filler 104, resulting in the wound filler 104 having the tissue in-growth 114. In the event the wound filler 104 has the tissue in-growth 114, the wound filler 104 may tear when the wound filler 104 is removed from the tissue site 106, leaving behind the one or more residual portions 102 of the wound filler 104. The one or more residual portions 102 of the wound filler 104 may not be readily visible to the human eye as the one or more residual portions 102 may be concealed by the tissue in-growth 114. In an alternative embodiment, the tissue site 106 may be of the nature that the treatment protocol uses several wound fillers (not shown). For example, large wounds that possess skin flaps or undermining may necessitate several wound fillers and may visually conceal the wound fillers once in place. In the event several wound fillers are placed in the tissue site 106 or the wound fillers are visually concealed by the tissue site 106, it becomes more likely that one of the wound fillers will be left in the tissue site 106.

The healthcare provider positions the scanner 112 over the tissue site 106 causing the scanner 112 to emit light in a wavelength that will excite the fluorescent markers 148 attached to the wound filler 104. In response to the one or more residual portions 102 of the wound filler 104 remaining in the tissue site 106 after the wound filler 104 has been removed, if any, the fluorescent markers 148 will produce visible light providing an indication that the one or more residual portions 102 of the wound filler 104 remain in the tissue site 106 and the location of the one or more residual portions 102 of the wound filler 104. Responsive to an indication that the one or more residual portions 102 of the wound filler 104 remain in the tissue site 106, the one or more residual portions 102 are removed from the tissue site 106.

In one embodiment, the wound filler 104 may be sized by the healthcare provider prior to positioning the wound filler 104 in the tissue site 106. The wound filler 104 is sized based on the dimensions of the tissue site 106. The wound filler 104 may be sized by cutting.

In response to an indication that the tissue site 106 is clear of the wound filler 104, a new wound filler treated with a coating agent (not explicitly shown), i.e., a second wound filler analogous to the first wound filler 104, may be placed in the tissue site 106 as determined by treatment protocol.

In another illustrative method of operation, the method may include treating the tissue site 106 of a patient with reduced pressure therapy. The wound filler 104 treated with a fluorescent dye is deployed proximate the tissue site 106. The wound filler 104 and a' portion of intact epidermis 140 are covered with the sealing member 126. The reduced-pressure interface 128 is fluidly coupled to the sealing member 126 such that the reduced-pressure interface 128 is in fluid communication with the wound filler 104 and the tissue site 106. The reduced-pressure source 142 is fluidly coupled to the reduced-pressure interface 128 and reduced pressure is applied to the wound filler 104. After a period of time, the wound filler 104 is removed from the tissue site 106. Using the scanner 112, the tissue site 106 is scanned to determine whether a portion of the wound filler 104 remains at the tissue site 106. Responsive to the one or more residual portions 102 of the wound filler 104 remaining at the tissue site 106, the one or more residual portions 102 are removed.

In another illustrative method of operation, the method may include positioning the wound filler 104 having a coating agent 108 containing fluorescent markers 148 proximate the tissue site 106. The wound filler 104 is removed after a time period. The tissue site 106 is scanned using the first mode of the scanner 112 to determine whether the residual portion 102 of the wound filler 104 remains at the tissue site 106. The first mode may emit a light greater than 600 lx and may be a pulsing mode. Responsive to a visual indication that the residual portion 102 of the wound filler 104 remains at the tissue site 106, the tissue site 106 is scanned using the second mode of the scanner 112. The second mode may emit a light less than 200 lx and may be a continuous mode. The residual portion 102 of the wound filler 104 is removed by a health care provider.

Figure 6:
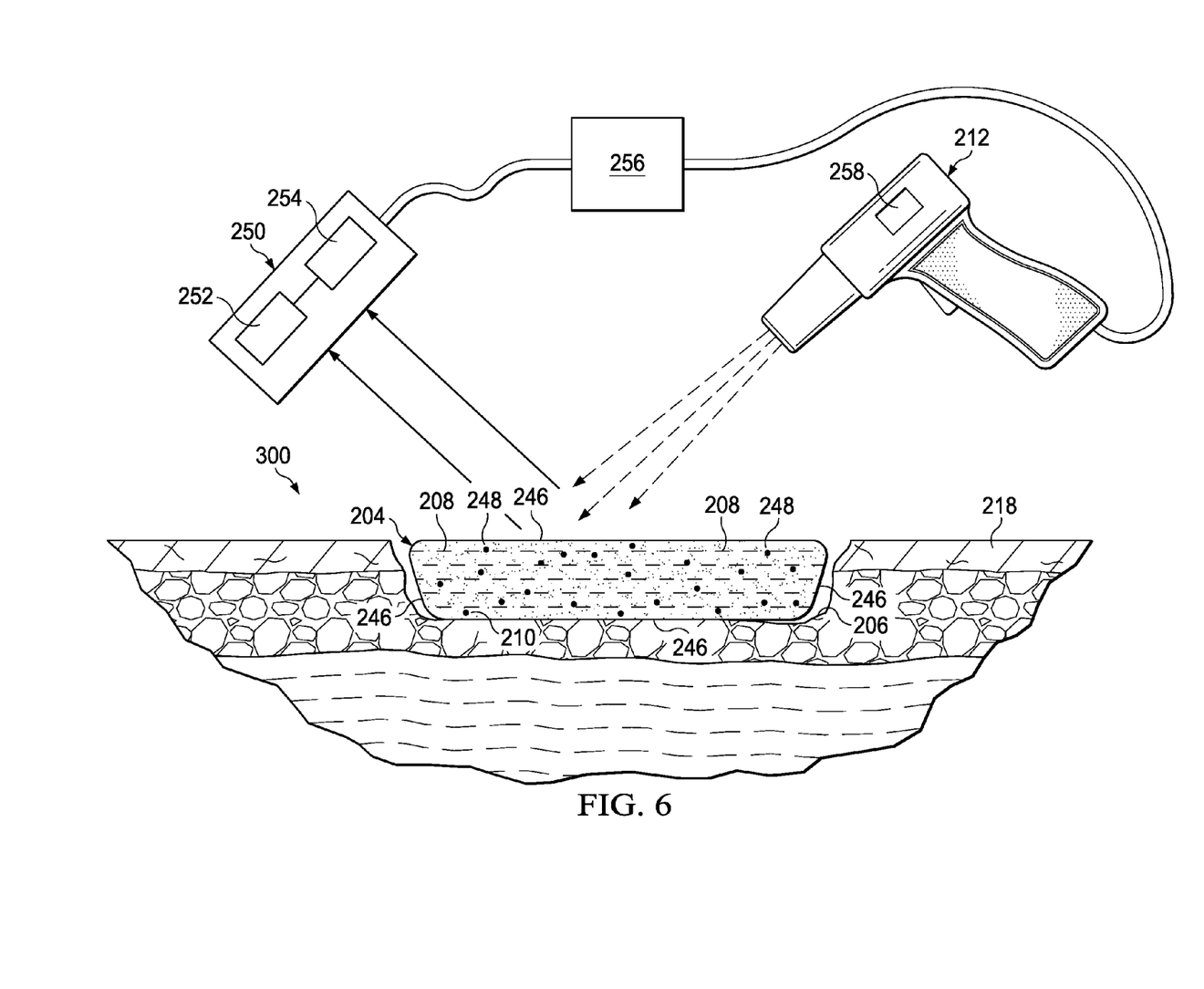
FIG. 6 is a cross sectional view (with a portion in perspective view) of another illustrative embodiment of a system for identifying residual portions of a wound filler left at a tissue site.

Referring now primarily to FIG. 6, a system 300 is presented for identifying one or more residual portions, e.g., residual portions 102 (FIG. 2) of a wound filler 204 that may be left at a tissue site 206. The system 300 is analogous in most respects to the system 100 of FIGS. 1-4, and accordingly, some parts are labeled with numerals indexed by 200 but not further described here. Among the differences, however, scanner 212 of system 300 includes additional features over the scanner 112 of system 100.

The system 300 includes the wound filler 204 treated with a coating agent 208 containing markers 210. The scanner 212 is operable to excite the markers 210 so that the markers 210 are detectable by a healthcare provider. The wound filler 204 is placed proximate the tissue site 206 as part of a process for treating the tissue site 206. One process for treating the tissue site 206 may include applying reduced pressure to the tissue site 206 using a reduced pressure treatment system such as reduced pressure treatment system 200 illustrated in FIG. 2. When using a reduced pressure treatment system, the wound filler 204 may also be a manifold to manifold reduced pressure to the tissue site 206.

The system 200 may be used with various different types of tissue sites 206. The tissue site 206 may be a wound or wound cavity. The tissue site 206 may be through an epidermis 218 and into a subcutaneous tissue or any other tissue.

As previously mentioned, the wound filler 204 is treated with the coating agent 208 containing the markers 210. The markers 210 may be fluorescent markers 248 that may be embedded or integrated throughout the wound filler 204. Additionally, the markers 210 may only extend a certain depth into the wound filler 204 from a surface 246 of the wound filler 204.

The scanner 212 may be a hand held device that is light weight and compact such that the scanner 212 is easily handled and moved by a healthcare provider. In one embodiment, the scanner 212 may be referred to as a fluorescence scanner. The scanner 212 emits light or electromagnetic radiation to excite or activate the fluorescent markers 248 into emitting light.

The scanner 212 includes, or may be connected to, a controller 256 and a receiver unit 250. The receiver unit 250 is configured to detect the light emitted by the excited or activated fluorescent markers 248. The receiver unit 250 includes a photodetector 252 for detecting the light emitted by the fluorescent markers 248 and an analog-to-digital converter 254 connected to the photodetector 252. The analog-to-digital converter 254 is in communication with the controller 256. In one embodiment, the receiver unit 250 and the controller 256 may be located on or within the scanner 212. The controller 256 synchronizes the scanner 212 and the receiver unit 250. The scanner 212 is timed to emit light at a certain frequency, and the controller 256 ensures that the receiver unit 250 is synchronized with the timing and frequency of the light emitted by the scanner 212. The controller 250 is configured to synchronize the scanner 212 and the receiver unit 250 in real time. The scanner 212 further includes, or is connected to, an indicator 258 that is in communication with the receiver unit 250. The indicator 258 may provide an audio or visual indication, detectable by a healthcare provider, when light from the fluorescent markers 248 is detected by the receiver unit 250.

Similar to the scanner 112, the scanner 212 may be configured to have two different modes of operation. The first mode may be a pulsing mode. The pulsing mode causes the scanner 212 to emit a pulsing light. Pulsing the light emitted from the scanner 212 may allow the scanner 212 to emit brighter light than light that is continuously emitted without damaging the scanner 212. In one illustrative, non-limiting embodiment, the light is pulsed between about 0.5 to 2 Hertz (Hz). In another illustrative, non-limiting embodiment, the light is pulsed at about 1 kHz. The light is pulsed at a frequency not commonly found in the environment the scanner 212 is operating to provide a contrast between environmental light frequencies and the light frequencies emitted by the activated fluorescent markers 248. To provide context, overhead lights and computer screens may commonly emit light with a frequency of 60 Hz, 120 Hz, and 180 Hz.

Increasing the brightness of the light emitted from the scanner 212 typically correlates to the fluorescent markers 248 absorbing more energy. Typically, the more energy the fluorescent markers 248 absorb, the brighter the light the fluorescent markers 248 will emit. While the light emitted from the fluorescent markers 248 will typically be brighter when subjected to the pulsing light, the pulsing light emitted from the fluorescent markers 248 may be difficult to detect by the human eye due to the pulsing nature of the light. The scanner 212 may therefore be equipped with the receiver unit 250 configured to detect the light emitted from the fluorescent markers 248.

The sensitivity of the receiver unit 250 may be adjustable to include or exclude certain sizes or concentrations of the fluorescent markers 248 based on the light emitted by the fluorescent markers 248. The sensitivity of the receiver unit 250 may be adjusted so that certain sizes or concentrations of the fluorescent markers 248 below a threshold level may be ignored. In some instances, it may be more harmful to attempt to remove fluorescent markers 248, which may or may not be attached to the residual portions 202 of the wound filler 204, than to leave the fluorescent markers 248 in place. For example, if the fluorescent marker 248 is no longer attached to the residual portion 202 of the wound filler 204 or the residual portion 202 is minute, then it could cause more harm than good to disturb the tissue site 206. Additionally, the sensitivity of the receiver unit 250 may be adjustable to exclude certain light frequencies based on the light frequency emitted by the scanner 112.

The second mode may be a continuous mode. The continuous mode causes the scanner 212 to emit a continuous light. In one embodiment, the continuous mode may cause the scanner 212 to emit the continuous light at less than 200 lx with a wavelength in the range of 700 nm to 900 nm. The pulsing light emitted in the first, pulsing mode will generally be brighter and contain more energy than the continuous light. The fluorescent markers 248 will absorb the continuous light emitted from the scanner 212 and, in return, emit a continuous light. The continuous light emitted from the fluorescent markers 248 may be easier for a heath care provider to see.

In one embodiment, the scanner 212 is adapted to excite the markers 210 to emit light in the non-visual range. The scanner 212 is adapted to detect the light emitted from the markers 210 and emit an audible or visual indication that the tissue site 206 contains the one or more residual portions 202 of the wound filler 204. The receiver unit 250 may detect light emitted from the markers 210, and the indicator 258 may emit an audible or visual indication that the tissue site 206 contains one or more residual portions 202 of the wound filler 204.

While various light sources are referenced herein to make items fluoresce, it should be understood that a range of light waves may be used. Infrared is one way. Blue or green lights are others. Still other colored light may be used.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for identifying a portion of a wound filler left at a tissue site, the system comprising:
a scanner configured to emit light having a first wavelength;
a wound filler treated with a coating agent, wherein the coating agent is operable to absorb light from the scanner and emit light having a second wavelength different from the first wavelength;
a receiver unit connected to the scanner for detecting light emitted by the coating agent;
a controller connected to the scanner and the receiver unit for managing the scanner and the receiver unit based on scanner settings and a feedback from the receiver unit; and
an indicator connected to the controller, the indicator operable to provide a visual or audio indication when the receiver unit detects the light emitted by the coating agent.

2. The system of claim 1, wherein the wound filler is a manifold adapted to distribute a reduced pressure to the tissue site.

3. The system of claim 1, wherein the coating agent is an ultraviolet dye and the scanner is an ultraviolet scanner.

4. The system of claim 1, wherein the coating agent is an infrared dye and the scanner is an infrared scanner.

5. The system of claim 1, wherein the coating agent is applied to a surface of the wound filler.

6. The system of claim 1, wherein the coating agent is at least partially embedded within the wound filler.

7. The system of claim 1, wherein the scanner has a first mode and a second mode.

8. The system of claim 7, wherein the first mode is a pulsing mode timed to emit light at a specific frequency and the second mode is a continuous mode to emit continuous light.

9. The system of claim 4, wherein the fluorescence scanner is configured to emit infrared light with wavelengths in a range of about 700 nm to 900 nm.

* * * * *